United States Patent
Chung

(10) Patent No.: US 9,271,823 B2
(45) Date of Patent: *Mar. 1, 2016

(54) URETERAL STENT

(75) Inventor: Steven Y. Chung, Ottawa, IL (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 277 days.

This patent is subject to a terminal disclaimer.

(21) Appl. No.: 13/466,809

(22) Filed: May 8, 2012

(65) Prior Publication Data

US 2012/0221117 A1 Aug. 30, 2012

Related U.S. Application Data

(63) Continuation of application No. 12/333,461, filed on Dec. 12, 2008, now Pat. No. 8,192,500.

(51) Int. Cl.
*A61F 2/04* (2013.01)
*A61M 27/00* (2006.01)

(52) U.S. Cl.
CPC .............. *A61F 2/04* (2013.01); *A61M 27/008* (2013.01); *A61F 2002/048* (2013.01); *A61F 2220/005* (2013.01); *A61F 2220/0033* (2013.01); *A61F 2250/0018* (2013.01); *A61F 2250/0019* (2013.01); *A61F 2250/0029* (2013.01); *A61F 2250/0039* (2013.01); *A61F 2250/0056* (2013.01); *A61F 2250/0098* (2013.01)

(58) Field of Classification Search
CPC ... A61F 2002/048; A61F 2/04; A61M 27/008
USPC ................ 604/8; 623/23.64–23.66, 23.7
See application file for complete search history.

(56) References Cited

U.S. PATENT DOCUMENTS 3,995,642 A * 12/1976 Adair ................................ 604/8
4,671,795 A * 6/1987 Mulchin ........................ 604/530
4,876,126 A 10/1989 Takemura et al.
(Continued)

FOREIGN PATENT DOCUMENTS

WO WO 2005096991 A1 * 10/2005 ............... A61F 2/04
WO WO 2007001992 A2 * 1/2007 ............ A61M 25/00

OTHER PUBLICATIONS

"Glidewire GuJdewires—For Ureteral Access, Passage, and Reduced Trauma", Boston Scientific, Technical Information, Copyright 2004, retrieved from www.bostonscientific.com,'urology, 4 pages.*

(Continued)

*Primary Examiner* — Andrew Iwamaye
(74) *Attorney, Agent, or Firm* — Kacvinsky Daisak Bluni PLLC

(57) ABSTRACT

A ureteral stent comprising a short renal coil made of a pliable material and a wick portion made of a material having a hydrophilicity or hydrophobicity different from that of the renal coil and extending from a ureteropelvic junction to a bladder so as to assist in the transfer of urine out of a kidney and into the bladder and to improve patient comfort. Due to increased hydrophilicity or hydrophobicity, wick may be significantly smaller in diameter than renal coil, resulting in less reflux of urine into the kidney and further decreasing patient discomfort. The stent may further comprise one or more couplers between the renal coil and wick portion, and the wick portion may comprise a sheath surrounding an elastic core to prevent kinking and enhance the ability of the wick portion to move with the patient. A method of ureteral stent placement is also disclosed.

8 Claims, 3 Drawing Sheets

(56) References Cited

U.S. PATENT DOCUMENTS

| | | | |
|---|---|---|---|
| 4,925,445 A | 5/1990 | Sakamoto et al. | |
| 4,931,037 A * | 6/1990 | Wetterman | 604/8 |
| 5,059,169 A | 10/1991 | Zilber | |
| 5,141,502 A | 8/1992 | Macaluso | |
| 5,176,626 A | 1/1993 | Soehendra | |
| 5,234,456 A | 8/1993 | Silvestrini | |
| 5,242,428 A | 9/1993 | Palestrant | |
| 5,334,166 A | 8/1994 | Palestrant | |
| 5,363,847 A * | 11/1994 | Viera | 600/434 |
| 5,401,257 A | 3/1995 | Chevalier | |
| 5,599,291 A | 2/1997 | Balbierz et al. | |
| 5,647,843 A | 7/1997 | Mesrobian et al. | |
| 5,772,640 A | 6/1998 | Modak et al. | |
| 6,332,892 B1 | 12/2001 | Desmond et al. | |
| 6,582,472 B2 | 6/2003 | Hart | |
| 6,620,202 B2 | 9/2003 | Bottcher et al. | |
| 6,652,569 B1 * | 11/2003 | Taylor et al. | 623/1.11 |
| 6,656,146 B1 | 12/2003 | Clayman et al. | |
| 6,676,623 B2 | 1/2004 | Whitmore | |
| 6,676,624 B2 | 1/2004 | Gellman | |
| 6,719,804 B2 | 4/2004 | St. Pierre | |
| 6,764,519 B2 | 7/2004 | Whitmore, III | |
| 6,908,447 B2 | 6/2005 | McWeeney et al. | |
| 6,913,625 B2 | 7/2005 | Segura et al. | |
| 6,929,664 B2 | 8/2005 | Kolb | |
| 6,945,950 B2 | 9/2005 | Clayman et al. | |
| 6,991,614 B2 | 1/2006 | McWeeney et al. | |
| 7,037,345 B2 | 5/2006 | Bottcher et al. | |
| 7,041,139 B2 | 5/2006 | Bluni et al. | |
| 7,217,250 B2 | 5/2007 | Kolb | |
| 7,291,180 B2 | 11/2007 | St. Pierre | |
| 7,316,663 B2 | 1/2008 | Whitmore, III | |
| 7,713,308 B2 | 5/2010 | Amos et al. | |
| 8,192,500 B2 * | 6/2012 | Chung | 623/23.66 |
| 2002/0055787 A1 | 5/2002 | Lennox et al. | |
| 2003/0109930 A1 * | 6/2003 | Bluni et al. | 623/23.7 |
| 2003/0120261 A1 * | 6/2003 | Gellman | 604/544 |
| 2003/0163204 A1 | 8/2003 | Rix | |
| 2003/0171708 A1 | 9/2003 | Segura et al. | |
| 2003/0199805 A1 | 10/2003 | McWeeney | |
| 2004/0092857 A1 | 5/2004 | Clayman et al. | |
| 2004/0127996 A1 | 7/2004 | Reever | |
| 2004/0193092 A1 | 9/2004 | Deal | |
| 2006/0122707 A1 * | 6/2006 | McWeeney et al. | 623/23.7 |
| 2006/0253104 A1 * | 11/2006 | Pandey et al. | 604/540 |
| 2006/0264912 A1 | 11/2006 | McIntyre et al. | |
| 2006/0271202 A1 * | 11/2006 | Ward | 623/23.7 |
| 2008/0077250 A1 * | 3/2008 | Amos | 623/23.66 |
| 2009/0306546 A1 * | 12/2009 | Knapp | 600/585 |
| 2010/0152861 A1 | 6/2010 | Chung | |
| 2012/0265020 A1 * | 10/2012 | Pandey et al. | 600/206 |

OTHER PUBLICATIONS

"Contour VL Variable Length Percuflex Stents with Hydroplus Coating", Boston Scientific Corporation, Technical Information, Copyright 2002, retrieved from www.bostonscientific.com, 1 page.

"Giidewire Guidewires—For Ureteral Access, Passage, and Reduced Trauma", Boston Scientific, Technical Information, Copyright 2004, retrieved from www.bostonscientific.com/urology, 4 pages.

Denstedt, Advances in Ureteral Stent Design, article, Jul. 23, 2007, Renal Stone Disease, 1st Annual International Urolithiasis Research Symposium, 6 pages.

\* cited by examiner

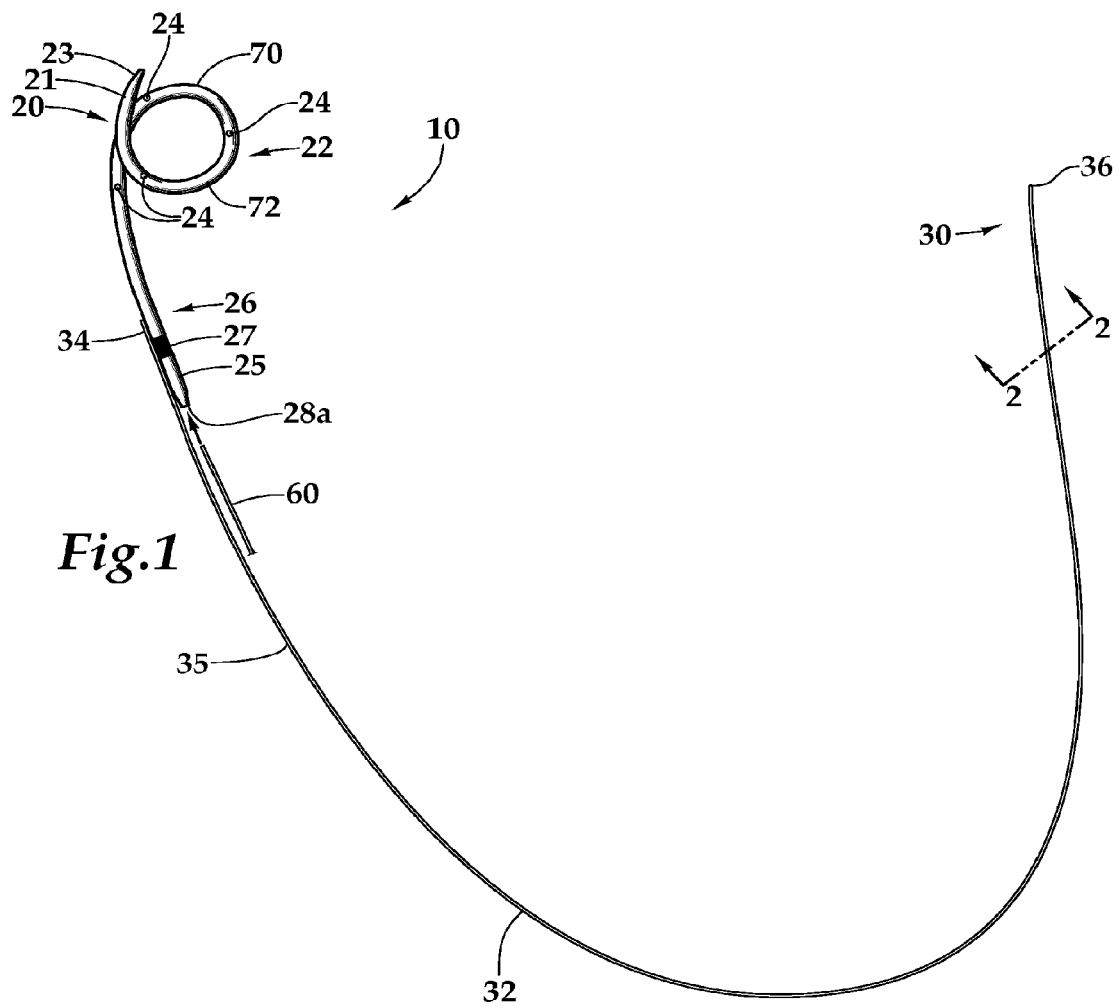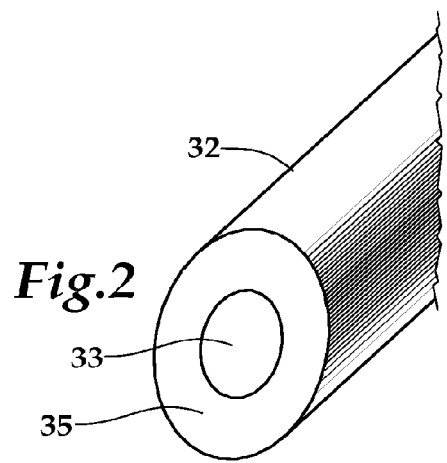

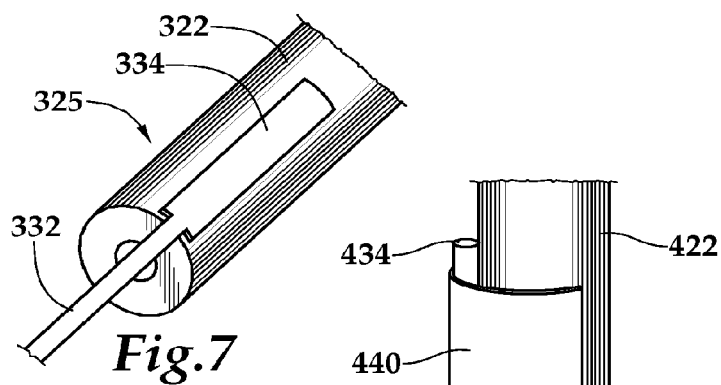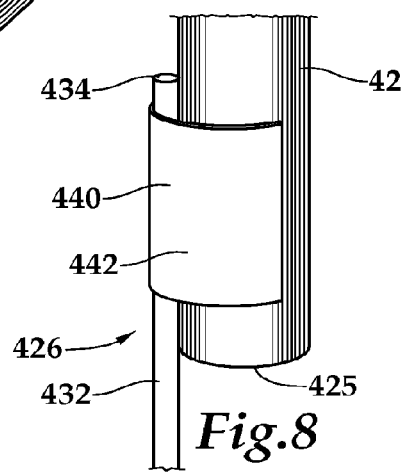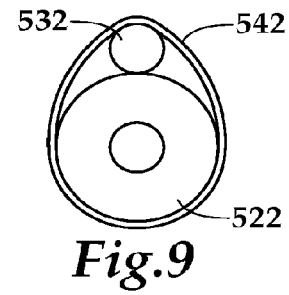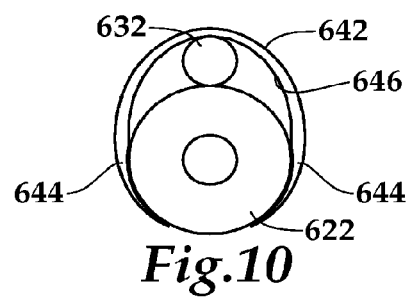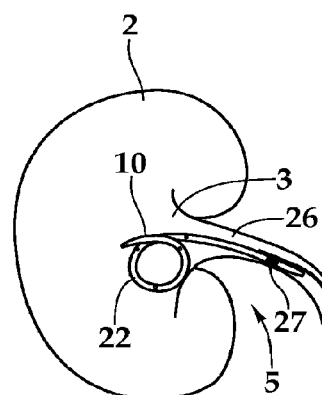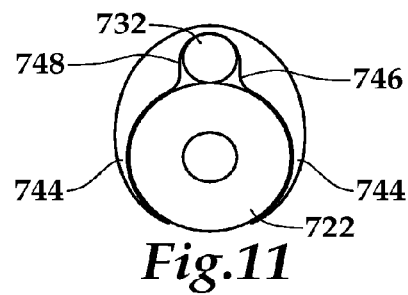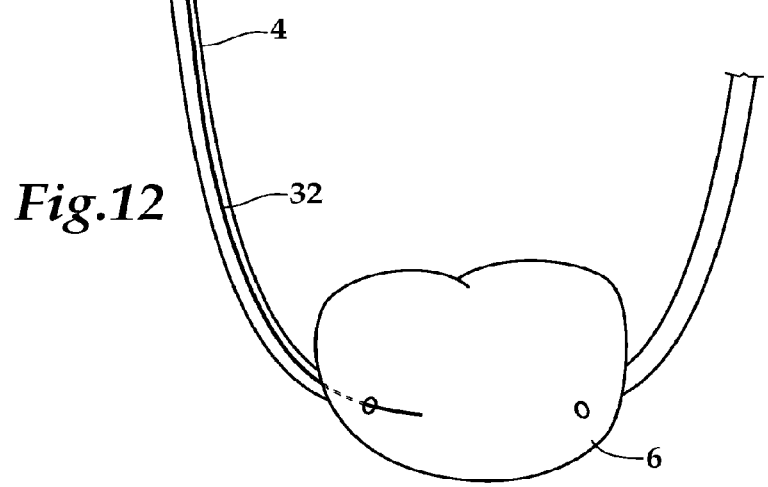

URETERAL STENT

CROSS-REFERENCE TO RELATED MATTERS

This application is a continuation of, and claims priority to, U.S. Nonprovisional application Ser. No. 12/333,461, filed on Dec. 12, 2008, entitled "URETERAL STENT" (now U.S. Patent No. 8,192,500), which is incorporated herein by reference in its entirety.

FIELD OF THE INVENTION

The present invention is directed to an improved stent, for example a ureteral stent.

BACKGROUND

A ureteral stent is used to aid in transfer of urine from one of a patient's kidneys to the patient's bladder where obstructions or other conditions may inhibit normal flow, typically by creating a path around a blockage. While the stent is used to allow for free flow of urine, the stent itself should stay in place and not migrate out of or further into the kidney, or out of or further into the bladder.

In the past, ureteral stents consisted of hollow tubes having spirals or loops at both ends. The spirals caused both ends of the stent to deviate from a generally linear or tubular shape, forming structures that would less easily lead to migration of the stent. In addition, in these stents, urine would flow through the center of the tube, while the walls of the tube prevented obstructions from blocking the flow. These tubes often were designed to be as large as possible allow urine to flow more freely.

Attempts to modify the traditional tube design have included changing the shape of the ends of the stent in an attempt to even further inhibit migration.

Other attempts have involved replacing the bladder end of the stent with highly flexible strands or loops so as to reduce the size of the stent in the bladder end in an attempt to decrease the discomfort felt by a patient. In these designs, the stent may resemble a traditional tubular stent starting at the renal end and progressing for a significant distance, e.g., about 12 cm, or such a distance as to start the flexible strands or loops at about the iliac vessels of the patient. This significant distance was employed to further enhance migration of the stent. Stents of this type suffer from the problem that stents of multiple sizes must be created and then a physician must select what size stent to use based on approximations of the patient's physiology. In addition, even with the reduced size of the strands or loops, significant patient discomfort may result.

What is needed is a ureteral stent that overcomes the drawbacks described above.

SUMMARY

In one aspect of the invention, a ureteral stent, comprising a renal coil at a renal end; a wick portion coupled to the renal coil and extending from an intersection with the renal coil to a bladder end; wherein the wick portion may be more rigid than the renal coil in a proximate end of the wick portion, proximate the renal coil, decreasing in rigidity or stiffness along the length of the wick portion, and the wick portion has significant hydrophilicity or hydrophobicity as compared to that of the renal coil. The renal coil may have a length from a tapered proximal end to a tapered distal end such that the distal end is located proximate a ureteropelvic junction of a patient when the renal coil is inserted into a kidney of a patient with the aid of a guidewire. In addition, the wick portion further may comprise a core and a sheath, the core comprising a material having an elasticity greater than an elasticity of the sheath.

The stent may further comprise a coupler joining the renal coil to the wick portion, and the coupler may one or more of: at least one clamp, a receiver in a distal end of said renal coil, sutures and/or an adhesive. The renal coil and wick may also be one continuous member of the same hydrophilic or hydrophobic material.

In another aspect of the invention, a ureteral stent comprising a renal end and a bladder end; a renal coil at the renal end, the renal coil having a proximal end, a distal end and a length therebetween; a wick portion extending from proximate the distal end to the bladder end, the wick portion comprising a hydrophilic or hydrophobic material; and/or a coupler joining the renal coil to the wick portion; wherein the length of the renal coil is such that when the stent is inserted in a patient, the distal end is located proximate a ureteropelvic junction. In addition, the renal coil may comprise a curved portion having a bottom spaced from the distal end by a distance along the renal coil of between about 0.3 cm and about 1.5 cm. Moreover, the wick portion may have an outside diameter between about 1 Fr. and about 3 Fr.

These and other features and advantages are evident from the following description of the present invention, with reference to the accompanying drawings.

BRIEF DESCRIPTION OF THE DRAWINGS

FIG. 1 is a side view of one embodiment of a ureteral stent.
FIG. 2 is a sectional view of a wick portion, taken through plane 2-2 in FIG. 1.
FIG. 7 is a perspective view of yet another embodiment of an intersection of portions of a ureteral stent.
FIG. 8 is a perspective view of still another embodiment of an intersection of portions of a ureteral stent.
FIG. 9 is a section view of another embodiment of an intersection of portions of a ureteral stent showing one type of possible coupler.
FIG. 10 is a section view of yet embodiment of an intersection of portions of a ureteral stent showing another type of possible coupler.
FIG. 11 is a section view of still another embodiment of an intersection of portions of a ureteral stent showing yet another type of possible coupler.
FIG. 12 is a schematic showing one possible installation of a ureteral stent in a urinary tract of a patient.

DETAILED DESCRIPTION

Figure 3:
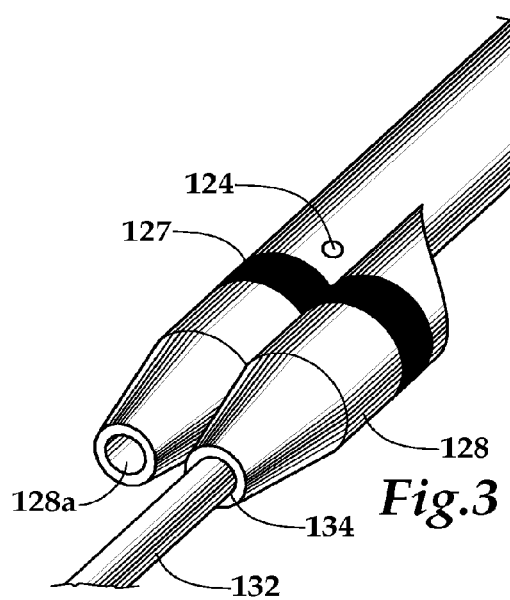
FIG. 3 is a perspective view of one embodiment of an intersection of portions of a ureteral stent.
Figure 4:
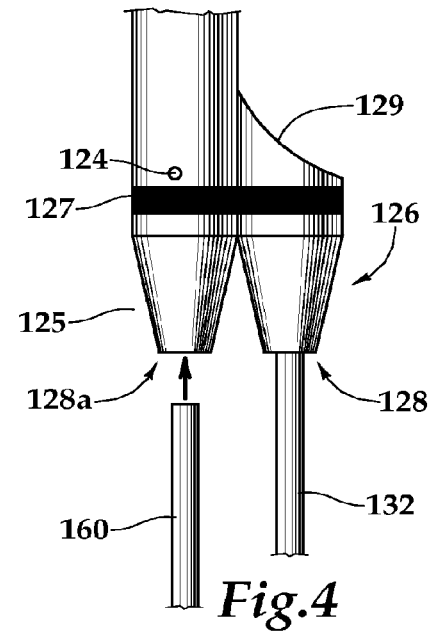
FIG. 4 is a side view of the embodiment of FIG. 3.

As seen in FIG. 1, a stent such as ureteral stent 10 comprising a renal coil 22 at a renal end 20 and wick portion 32 extending from renal coil 22 to a bladder end 30.

Renal coil 22 may comprise a flexible coiled material such as a rubberized or polymerized material. As its name implies, renal coil 22 may be coiled at renal end 20 of stent 10 for locating and maintaining renal end 20 inside kidney 2, preferably proximate renal pelvis 3. Renal coil 22 may be spiral shaped or generally J-shaped, or it may have other configurations that will keep renal end 20 from migrating out of kidney 2. Moreover, renal coil 22 may have a tapered end 23 at the proximal end of stent 10, which may facilitate insertion of stent 10. Furthermore, renal coil 22 may have a tapered end 25 for ease of stent 10 removal.

In addition, renal coil 22 may be a generally tubular material having an outer diameter of between about 3 Fr. and about 10 Fr., preferably between about 5 Fr. And about 7 Fr., and in one embodiment about 6 Fr. A thicker diameter renal coil 22 may prevent movement of coil 22 from kidney 2 into ureter 4 and/or bladder 6. However, a thicker coil 22 may also provide more discomfort for a patient.

Renal coil 22 may be generally hollow proximate intersection 26 with wick portion 32 so as to provide an opening or receiver 28a for a guide wire 60. In the embodiment shown in FIG. 1, renal coil 22 may be generally hollow along its length, which may make manufacture of renal coil 22 easier as renal coil 22 may be formed from a length of hollow tubing without requiring additional manufacturing steps. Inside diameter may be between about V2 Fr. and about 3 Fr., preferably between about 1 Fr. And about 2 Fr., and in one embodiment about 1 V2 Fr or about 0.038 inches.

Renal coil 22 may further comprise a plurality of markings 24 spaced generally equidistantly from one another. Markings 24 may comprise a series of holes axially spaced along a length of renal coil 22. In addition, a radioopaque mark 27 may be circumferentially placed around a perimeter of coil 22 at the distal end 25 of coil 22, as seen in FIG. 1. Mark 27 may be visible to a physician under X-ray, e.g., when viewed during insertion of stent 10. In this way, the physician may use mark 27 to determine placement of renal coil 22 within kidney 2.

To insert stent 10 in a patient, proximal end 21 of renal coil 22 may be placed over a long guidewire 60 that traverses bladder 6, ureter 4 and resting in kidney 2. Guidewire 60 may extend substantially along the length of renal coil 22, from distal end 25 to proximal end 21, causing renal coil 22 to take on a generally linear shape.

A pusher may be placed over the guidewire 60 behind the stent 10. Pusher may be between about 4 Fr. and about 5 Fr. in diameter and about 100 cm in length, although other dimensions are possible for pusher. In one embodiment, a ureteral catheter having a diameter of about 5 Fr. and a length of about 120 cm may be used as a pusher.

The Pusher may exert an axial force on distal end 25 of renal coil 22 and may be used to place the distal end 25 of renal coil 22 proximate to ureteropelvic junction 5. While stent 10 is being inserted, the pusher may be alongside wick 32 from distal end 36 up to the level of ureteropelvic junction 5. Once an appropriate position for stent 10 is determined, guidewire 60 may be removed first, which may cause renal coil 22 to lose its generally linear shape. As renal coil 22 loses its generally linear shape and forms a loop or pigtail 70, the pusher also may be removed, which may leave stent 10 in its desired configuration and in its desired location.

Turning to FIG. 12, stent 10 preferably is inserted such that renal coil 22 is located within kidney 2 and/or renal pelvis 3 with intersection 26 proximate ureteropelvic junction 5. To assist in this placement, physician may rely on mark 27, as described above. In addition, renal coil 22 may be sized such that enough of coil 22 is within kidney 2 and/or renal pelvis 3 to keep stent 10 from migrating out of kidney 3. At the same time, renal coil 22 may be sized so as to minimize the amount of renal coil 22 extending beyond ureteropelvic junction 5 and into ureter 4, which may increase patient comfort. As such, renal coil may be between about 1 cm and about 9 cm long, preferably between about 2 cm and about 8 cm long, still more preferably between about 2 cm and about 5 cm long.

Renal coil 22 may form a curved portion 70 such as a loop or other structure that causes coil 22 to depart from its generally linear shape moving from distal end 25 to proximal end 21. Loop 70 may have a bottom 72 that may rest against, abut or otherwise contact kidney 2 to prevent stent 10 from inadvertently migrating out of kidney 2 after stent 10 is installed. Bottom 72 may be spaced from distal end 25 of renal coil 22 by a distance along renal coil 22 of between about 0.2 cm and about 2 cm, preferably between about 0.3 cm and about 1.5 cm, still more preferably between about 0.5 cm and about 1 cm, and in one embodiment, about 0.7 cm.

Turning back to FIG. 1, stent 10 further comprises wick portion 32. Wick portion 32 may comprise a single strand of material from proximal end 34 to distal end 36. Wick portion 32 may comprise a relatively slender, relatively hydrophilic or hydrophobic material. As such, small diameter may ease patient discomfort by providing a minimally intrusive medium for conveying urine from kidney 2 to bladder 6. In addition, hydrophilic or hydrophobic material may facilitate wicking of urine from kidney 2 to bladder 6, further easing patient discomfort by decreasing surface tension along wick portion 32. This decreased surface tension may also reduce and/or generally eliminate reflux of urine through ureter 4 back into kidney 2.

Wick portion 32 may have a generally constant diameter from proximal end 34 to distal end 36. However, proximal end 34 may have variations in shape for coupling with renal coil 22, as will be described in greater detail below. Wick portion 32 may have a diameter of between about V2 Fr. and about 6 Fr., preferably between about 1 Fr. and about Fr., still more preferably between about 1 Fr. and about 3 Fr., and in one embodiment about 1 Fr.

In addition to being relatively narrow and hydrophilic or hydrophobic, wick portion 32 may be significantly more rigid or stiff than renal coil 22 at its proximal end 34 and significantly more flexible and less rigid than renal coil 22 proximate its distal end 36. However, despite its rigidity at its proximal end 34, wick portion 32 preferably is not so rigid as to cause wick portion 32 to be substantially columnar since stent 10 requires flexibility to move along curves of ureter 4 and to move with patient as patient moves, i.e., to negotiate tortuosity of the ureter 4. Wick portion 32 may have a core 33 and a sheath 35, the core 33 comprising an elastic material that resists deformation. This may decrease trauma to a patient since elastic material may inhibit plastic deformations of wick portion 32, which deformations may press along wall of ureter 4 and/or inhibit flow of urine into bladder 6. In one example, wick portion 32 may be made of a material such as GLIDEWIRE, manufactured by Terumo Corporation. Acceptable properties of wick portion may be described in U.S. Pat. No. 4,876,126 to Takemura, et al. and U.S. Pat. No. 4,925,445 to Sakamoto, et al., the contents of which are both incorporated herein by reference. In another embodiment, wick 32 may also be made of polymer or other soft material with or without sheath and inner core.

Decreased diameter and increased hydrophilicity or hydrophobicity contribute to decreasing patient discomfort and more than offset any increase in discomfort that may be experienced due to increased rigidity. In addition, increased rigidity and/or hydrophilicity or hydrophobicity allow renal coil 22 to be shorter than otherwise may be necessary because rigidity and/or hydrophobicity or hydrophobicity prevent wick portion 32 from migrating upward into kidney 2.

Renal coil 22 and wick portion 32 may meet at intersection 26. As seen in FIGS. 3-6, renal coil 22 and wick portion 32 may be joined at intersection 26 in a number of ways. For example, as seen in the embodiment of FIG. 3, renal coil 122 may comprise a plurality of tapered openings or receivers 128 at a tapered distal end 125. One receiver 128 may be sized and positioned to accommodate a proximal end 134 of wick portion 132 while a second receiver 28a may be sized and positioned to accommodate a guide wire 160 for installing stent 110. Since wick portion 132 may be approximately the same size as guide wire 160, receivers 128, 128a may be approximately equally sized and similarly tapered. However, receiver 128 may be slightly smaller than receiver 128a in order to allow for an interference fit between renal coil 122 and wick portion 132. Conversely, receiver 128a may be slightly larger than receiver 128 so as to prevent an interference fit between guide wire 160 and receiver 128a, thereby allowing for easier removal of guide wire 160 after installation of stent 110.

Receiver 128a may be generally coaxial with a remainder of renal coil 122 such that guide wire 160 may exert a substantially axial force on renal coil 122 during installation. In this embodiment, renal coil 122 may be generally hollow along its length. This may allow guide wire to extend substantially along a length of renal coil 122 during installation. As such, renal coil 122 may be generally straight during installation, facilitating transport through ureter 4 and reducing patient discomfort.

In another embodiment, receiver 128a may have a predetermined depth from distal end 125 to a closed end of receiver 128a at a point along length of renal coil 122. This configuration may result in less of renal coil 122 being elongated or straightened prior to insertion of stent 110. However, this configuration also provides a surface against which guide wire 160 may push, which may make installation of stent easier for the physician.

Figure 5:
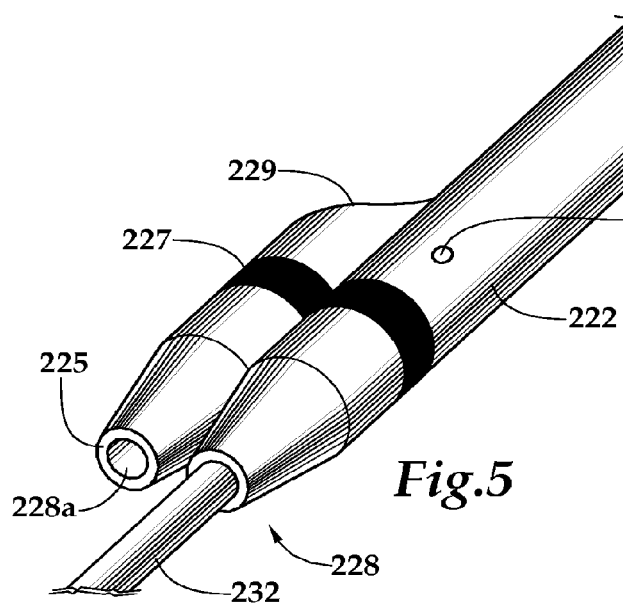
FIG. 5 is a perspective view of another embodiment of an intersection of portions of a ureteral stent.
Figure 6:
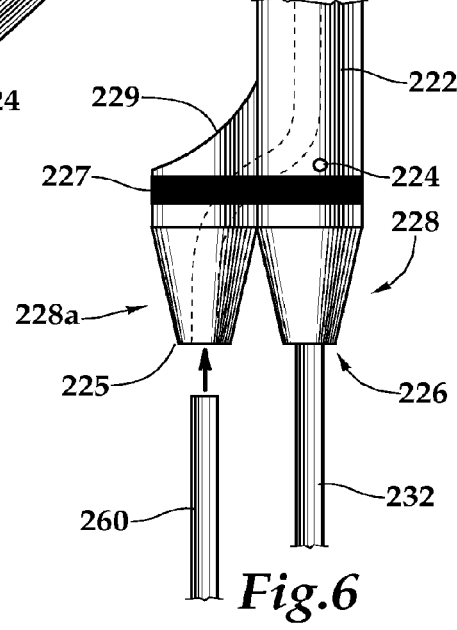
FIG. 6 is a side view of the embodiment of FIG. 5.

In yet another embodiment, shown in FIGS. 5 and 6, receiver 228 for wick portion 232 may be generally coaxial with renal coil 222, while receiver 228a may be offset. In this embodiment, receiver 228a may extend along a length of renal coil 222. However, receiver 228a may have a predetermined length substantially smaller than the length of renal coil 222. In addition, in this embodiment, receiver 228 for wick 232 may have a closed end a predetermined distance from distal end 223, and receiver 228a for guidewire 260 may continue above closed end of receiver 228 and extend toward proximal end 221 of renal coil 222. One example of the path of receiver 228a, which reflects the path glidewire 260 may take, is represented by the dashed lines in FIG. 6.

In this case, external surface of receiver 228a may taper at its closed end 229. This taper may have several benefits. First, it may create a transition in thickness of renal coil 222 instead of a step-type increase. As outer surface tapers, this may allow renal coil 222 to move more freely and comfortably through ureter 4, for example, by providing a ramp surface that may slide along ureter wall if renal coil 222 were to contact ureter wall. Second, taper may form a thicker wall opposite from opening of receiver 228a, which may inhibit guidewire 260 from piercing renal coil 222 or may direct non-axial forces applied by guidewire 260 toward renal coil 222 instead of away from it, which may further aid in insertion of stent 10.

Turning to FIG. 7, another possible connection between renal coil 22 and wick portion 32 is shown. (In these embodiments, as in the preceding ones, similar parts have similar reference numerals but varying 100s prefixes.) In the embodiment of FIG. 7, proximal end 334 of wick portion 332 may be flattened or otherwise deformed, e.g., by compressing proximal end 334 to form a segment of the perimeter of a cylinder. This segment may have a radius of curvature approximating that of the outside diameter of renal coil 322 such that proximal end 334 of wick portion 332 and distal end 325 of renal coil 322 substantially interface with one another. Alternatively, as seen in FIG. 1, proximal end 34 of wick portion 32 may be unmodified and may simply abut distal end 25 of renal coil. As a further possibility, proximal end 34 may be tapered at its tip to provide a ramp surface for sliding along wall of ureter 4 during installation, which may reduce patient discomfort.

To assist in coupling of renal coil 22 and wick portion 32, stent 10 may further comprise a coupler 440, as shown in FIG. 8. Coupler 440 may comprise one or more bands or clamps 442. Clamp 442 may be sized such that an interference fit is formed when renal coil 422 and wick portion 432 are placed within clamp 442. As seen in FIG. 9, clamp 542 may entirely surround renal coil 522. Alternatively, as seen in FIG. 10, clamp 642 may surround a portion of renal coil 622 and have a pair of spaced apart arms 644 defining a gap in between them. Interior surface 46 of clamp 42 may be generally curvilinear, or, as seen in FIG. 11, interior surface 746 may have a depression 748 for accommodating wick portion 732. Clamp 42 may be formed of a biologically acceptable material, including metal such as titanium, nickel, steel or surgical stainless steel or a plastic material such as polyethylene or polypropylene. Moreover, clamps 42 may be radioopaque to aid in placement of stent 10.

Alternatively, or in addition, coupler 40 may comprise one or more sutures 50. Preferably, sutures encircle renal coil 22 and wick portion 32 a plurality of times to maintain alignment of intersection 26 between wick portion 32 and renal coil.

Moreover, as another alternative or addition to the couplers 40 described above, wick portion 32 may be affixed to renal coil 22 at intersection 26 using an adhesive or bonding agent. For example, adhesive may be one or more of epoxy phenolic, thermoplastic, acrylic, cyanoacrylate, urethane, silicone and/or polyolefin.

Renal coil 22 and wick portion 32 preferably overlap at intersection 26. Overlapping intersection 26 may be minimized to reduce the width of stent 10 at intersection 26 since a narrower stent 10 may be less noticeable and more comfortable to a patient. Overlap may be between about ½ cm and about 4 cm, preferably between about 1 cm and about 3 cm, still more preferably between about 1.5 cm and about 2.5 cm, and in one embodiment, about 2 cm.

Since renal coil 22 may be sized so as to terminate proximate ureteropelvic junction 5, stent 10 may be modified for patients with different length ureters 4 by adjusting length of wick portion 32. As such, different length stents 10 may be manufactured so that a physician has the option, e.g., of choosing a small, medium or large stent 10. Alternatively, a longer stent 10 may be manufactured, which physician may be able to customize to an individual patient by trimming distal end 36 of wick portion 32. This may allow for greater customization of stent 10, further increasing comfort and/or decreasing trauma to a patient.

While the foregoing written description of the invention enables one of ordinary skill to make and use what is considered presently to be the best mode thereof, those of ordinary skill will understand and appreciate the existence of variations, combinations, and equivalents of the specific exemplary embodiment and method herein. The invention should therefore not be limited by the above described embodiment and method, but by all embodiments and methods within the scope and spirit of the invention as claimed.

What is claimed is:

1. A ureteral stent, comprising:
    a retention member having a distal end portion and a proximal end portion, the distal end portion of the retention member defining a first opening configured to receive a guidewire, the retention member having a diameter, the first opening extending along a first axis, the retention member having an external surface on an outer circumference of the retention member, the retention member being coiled at the proximal end portion and uncoiled at the distal end portion;

a receiver coupled to the external surface of the retention member, the receiver defining a second opening, the second opening extending along a second axis, the first axis being substantially parallel to the second axis; and a wick member including a strand of material, the wick member extending from the retention member, a proximal end portion of the strand of material being disposed within the second opening of the receiver, the strand of material of the wick member includes a core portion and a sheath coupled to the core portion, the wick member having a diameter, the diameter of the retention member being greater than the diameter of the wick member, wherein the proximal end portion of the strand of material of the wick member is more rigid than the retention member, and a distal end portion of the strand of material of the wick member is less rigid than the retention member.

2. The ureteral stent of claim 1, wherein the core portion is formed of a first material and the sheath portion is formed of a second material different than the first material.

3. The ureteral stent of claim 1, wherein the retention member defines a lumen extending from the proximal end portion of the retention member to the distal end portion of the retention member.

4. The ureteral stent of claim 1, wherein the retention member includes a tubular portion.

5. A ureteral stent, comprising:

a retention member having a distal end portion and a proximal end portion, the distal end portion of the retention member comprising a first receiver the first receiver definging a first opening configured to receive a guidewire, the retention member having a diameter, the first receiver extending along a first axis, the retention member having an external surface on an outer circumference of the retention member, the retention member forming a loop at the proximal end portion and a linear shape at the distal end portion;

a second receiver coupled to the external surface of the retention member, the second receiver defining a second opening, the second opening extending along a second axis, the first axis being substantially parallel to the second axis; and a strand of material extending from the retention member, a proximal end portion of the strand being disposed within the second opening of the second receiver, the strand includes a core portion and a sheath coupled to the core portion, the strand having a diameter, the diameter of the retention member being greater than the diameter of the strand, wherein the proximal end portion of the strand is stiffer than the retention member, and a distal end portion of the strand is more flexible than the retention member.

6. The ureteral stent of claim 5, wherein the core portion is formed of a first material and the sheath portion is formed of a second material different than the first material.

7. The ureteral stent of claim 5, wherein the retention member defines a lumen extending from the proximal end portion of the retention member to the distal end portion of the retention member.

8. The ureteral stent of claim 5, wherein the retention member includes a tubular portion.

\* \* \* \* \*